(12) United States Patent
Kishi et al.

(10) Patent No.: US 6,485,685 B1
(45) Date of Patent: Nov. 26, 2002

(54) PURIFYING AGENT, APPARATUS AND METHOD FOR FORMING PURIFYING AGENT, AND PURIFYING METHOD USING THE AGENT

(75) Inventors: Tomomi Kishi; Hisashi Nakano; Masatoshi Michibata, all of Toyota (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 09/194,754

(22) PCT Filed: Apr. 2, 1998

(86) PCT No.: PCT/JP98/01525

§ 371 (c)(1),
(2), (4) Date: Dec. 3, 1998

(87) PCT Pub. No.: WO98/44960

PCT Pub. Date: Oct. 15, 1998

(30) Foreign Application Priority Data

Apr. 4, 1997 (JP) .............................................. 9-087032

(51) Int. Cl.⁷ .......................... A61L 9/00; A61L 11/00; A62B 7/08; A01N 25/06; A01N 25/02
(52) U.S. Cl. .............................. 422/29; 422/5; 422/120; 422/122; 422/123; 422/186.07; 424/40; 424/43; 424/76.7
(58) Field of Search ..................... 422/5, 29, 120, 422/122, 123, 186.07; 424/40, 43, 76.7

(56) References Cited

U.S. PATENT DOCUMENTS

| | | | | |
|---|---|---|---|---|
| 4,072,613 A | * | 2/1978 | Alig | 210/198 R |
| 4,351,734 A | * | 9/1982 | Kauffman | 210/748 |
| 5,154,893 A | * | 10/1992 | Nakade | 422/124 |
| 5,207,993 A | * | 5/1993 | Burris | 422/256 |
| 5,213,773 A | * | 5/1993 | Burris | 422/256 |
| 5,292,479 A | * | 3/1994 | Haraga et al. | 422/5 |
| 5,387,400 A | * | 2/1995 | Pelster | 422/186.03 |
| 5,460,705 A | * | 10/1995 | Murphy et al. | 204/252 |
| 5,514,267 A | * | 5/1996 | Machiya et al. | 210/170 |
| 5,578,280 A | * | 11/1996 | Kazi et al. | 422/186.07 |

FOREIGN PATENT DOCUMENTS

| | | |
|---|---|---|
| JP | 62-50794 | 3/1987 |
| JP | 1-107766 | 4/1989 |
| JP | 1-70838 | 5/1989 |
| JP | 6-105893 | 9/1995 |
| JP | 7-232184 | 9/1995 |

\* cited by examiner

Primary Examiner—Robert J. Warden, Sr.
Assistant Examiner—Morgan R. Chorbaji
(74) Attorney, Agent, or Firm—Finnegan, Henderson, Farabow, Garrett & Dunner, L.L.P.

(57) ABSTRACT

A purifying agent or the like which can improve purifying performance is obtained. A container (12) of a purifying agent generating apparatus (10) contains a solution (14), into which a surface-active agent has been dissolved, and ozone gas is supplied thereto. In this way, a purifying agent (34) (i.e., aggregate of ozone-containing bubbles (32), each of which includes an ozone-containing membrane, into which ozone has been dissolved, and ozone-containing gas, which is contained in the inner portion of the membrane and includes ozone) is generated. Therefore, odor which fills a sealed space can be removed and a higher purifying performance is obtained.

7 Claims, 6 Drawing Sheets

◍ ········ H₂O (WATER)

◎ ········ O₃ (OZONE)

○ ········ O₂ OR THE LIKE (AIR)

○ ········ OZONE-CONTAINING BUBBLE
◎ ········ OZONE
○ ········ AIR
● ········ ODOR

F I G. 6
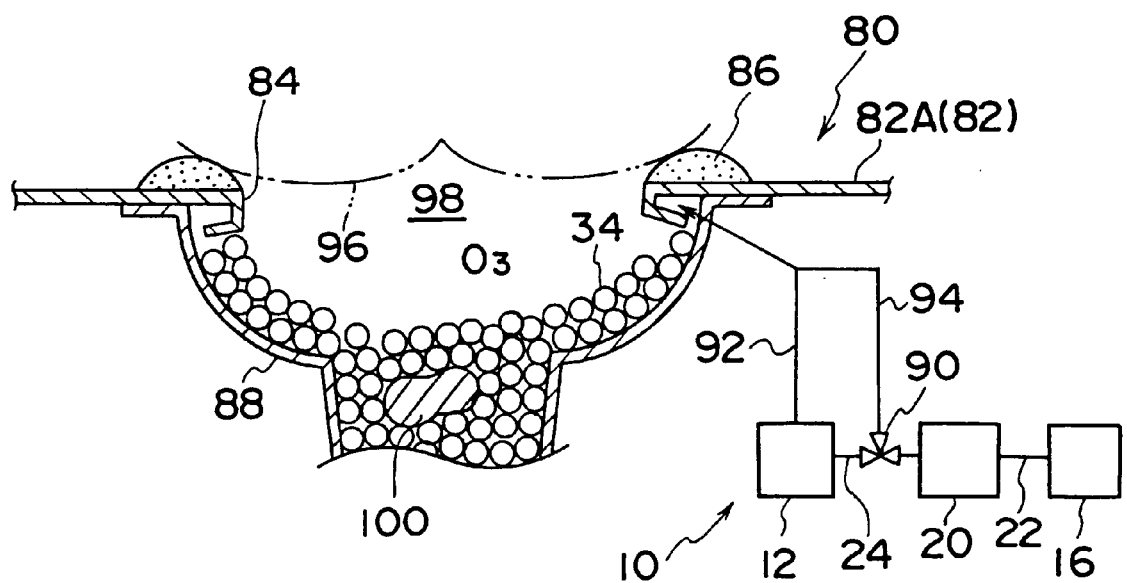

PURIFYING AGENT, APPARATUS AND METHOD FOR FORMING PURIFYING AGENT, AND PURIFYING METHOD USING THE AGENT

TECHNICAL FIELD

The present invention relates to a purifying agent which is suitable for deodorization/sterilization, an apparatus for and a method of manufacturing the purifying agent, and a purifying method using the purifying agent.

TECHNICAL BACKGROUND

Conventionally, a spray-type bubble generator which contains a purifying agent such as a deodorant or sterilizer is used against the odor or bacteria of a portable toilet, household garbage, or the like.

However, a deodorization/sterilization effect of bubbles applied by this type of bubble generator is achieved at only a portion which contacts the bubbles. Namely, the deodorization/sterilization function of the bubbles is achieved by deodorization/sterilization components contained within the bubble membranes contacting an object of deodorization/sterilization, and after the bubbles have disappeared, the deodorization/sterilization function of the bubbles is achieved by a solution including the bubble membranes attaching to or permeating through the object of deodorization/sterilization as a liquid. In other words, since gas (air) contained within the bubble membranes does not have any deodorization/sterilization action, the gas is merely discharged to a closed space within a facility or a space within a room.

For example, assuming that the bubbles are applied to an object of deodorization/sterilization within a portable toilet by using the above-described bubble generator, therein the initial stage of application, because layers of bubbles having a deodorization/sterilization function are formed on the surface of the object of deodorization/sterilization, the portion of the object which contacts the bubbles is deodorized/sterilized. Further, since the layers of bubbles are formed on the surface of the object of deodorization/sterilization, diffusion paths of odor from the object of deodorization/sterilization are blocked. As a result, after the layers of bubbles are formed, diffusion of odor from the object of deodorization/sterilization is prevented. Therefore, regarding these points, the deodorization/sterilization function of the purifying agent in the bubble generator is effectively achieved.

However, as mentioned above, since the gas (air) contained within the bubble membranes does not have any deodorization/sterilization action, odor which has been already generated and which has filled the portable toilet is not removed in the stages after the bubbles have disappeared. Therefore, regarding these points, the deodorization/sterilization function of the purifying agent in the bubble generator is not effective.

Sterilization performance is important. However, it is more desirable to develop a purifying agent also having deodorization performance which can remove such odor, i.e., a purifying agent whose purifying performance is further improved.

With the aforementioned in view, an object of the present invention is to obtain a purifying agent which has higher purifying performance, an apparatus for and a method of generating the purifying agent, and a purifying method using the purifying agent.

DISCLOSURE OF THE INVENTION

A first aspect of the present invention is a purifying agent which is formed by an aggregate of ozone-containing bubbles, each bubble having an ozone-containing membrane, into which ozone has been dissolved, and ozone-containing gas, which is contained in this ozone-containing membrane and includes ozone.

A second aspect of the present invention is an apparatus for generating a purifying agent, comprising: a container which contains a solution into which a surface-active agent has been dissolved; ozone gas generating means which generates ozone gas; and ozone gas supply means which communicates the ozone gas generating means and the inner portion of the container and supplies the ozone gas generated by the ozone gas generating means into the solution.

A third aspect of the present invention is a method of generating a purifying agent, comprising the step of: supplying ozone gas generated by ozone gas generating means into a solution which is contained within a container and into which a surface-active agent has been dissolved.

A fourth aspect of the present invention is a purifying method using a purifying agent, comprising the step of: effecting at least one of deodorization and sterilization on an object of deodorization/sterilization by using the purifying agent of the above-described first aspect.

A fifth aspect of the present invention is a purifying method using a purifying agent, comprising the step of: supplying the purifying agent formed by the aggregate of ozone-containing bubbles of the first aspect into a bowl of a toilet, and thereafter, further supplying ozone-containing gas to a space above the supplied purifying agent in the bowl.

In accordance with the first aspect of the present invention, when an object of deodorization/sterilization is covered with the aggregate of ozone-containing bubbles forming the purifying agent, diffusion paths of odor discharged from the object of deodorization/sterilization are blocked. Accordingly, the odor is not diffused.

Moreover, when each of the ozone-containing bubbles has disappeared, the ozone-containing membrane of the ozone-containing bubble is applied to and permeates through the object of deodorization/sterilization as ozone water having deodorization/sterilization action. Accordingly, the object of deodorization/sterilization is deodorized and sterilized.

Further, when each of the ozone-containing bubbles has disappeared, the ozone-containing gas which is contained within the ozone-containing membrane and has deodorization/sterilization action is released and diffused. As a result, the odor which has been already discharged from the object of deodorization/sterilization and has filled the surrounding space is deodorized by the ozone-containing gas.

Namely, in accordance with the present invention, deodorization/sterilization action comprising three processes, i.e., blocking of the diffusion paths of odor before the bubbles have disappeared, deodorization/sterilization action by the ozone water in the ozone-containing membrane after the bubbles have disappeared, and deodorization by the ozone-containing gas after the bubbles have disappeared, is obtained.

In accordance with the second aspect of the present invention, the purifying agent of the first aspect is generated as follows.

First, ozone gas is generated by the ozone gas generating means. Next, the ozone gas generated by the ozone gas supply means is supplied into the solution contained within the container. In this way, a portion of the ozone gas is dissolved into the solution, into which the surface-active agent has been dissolved, and the ozone gas which has not been dissolved into the solution goes up as it is toward the surface of the solution. As a result, the purifying agent of the first aspect (i.e., the aggregate of ozone-containing bubbles, each of which has an ozone-containing membrane and ozone-containing gas) is generated on the surface of the solution.

In the above-described generating process, the amount of ozone-containing bubbles generated, the size of each ozone-containing bubble, or the like can be arbitrarily controlled to the optimal amount, size, or the like by properly selecting the type and concentration of the surface-active agent and the amount of ozone gas supplied.

In accordance with the third aspect of the present invention, the ozone gas which has been generated by the ozone gas generating means is supplied into the solution which is contained within the container and into which the surface-active agent has been dissolved. In this way, the purifying agent of the first aspect (i.e., the aggregate of ozone-containing bubbles, each of which has an ozone-containing membrane and ozone-containing gas) is generated on the surface of the solution through the same process as the process described in the operation of the second aspect of the present invention.

In accordance with the fourth aspect of the present invention, at least one of deodorization and sterilization is effected on the object of deodorization/sterilization using the purifying agent of the first aspect (i.e., the aggregate of ozone-containing bubbles, each of which has an ozone-containing membrane and ozone-containing gas). In this way, the deodorization/sterilization action comprising three processes described in the operation of the first aspect is effectively achieved and effective deodorization/sterilization is carried out.

It is determined by a user as to whether the purifying method using the purifying agent relating to the present invention is used for the purpose of deodorization, sterilization, or both.

In accordance with the fifth aspect of the present invention, first, a predetermined amount of purifying agent formed by the aggregate of ozone-containing bubbles of the first aspect is supplied into the bowl of the toilet. In this way, the aggregate of ozone-containing bubbles is accumulated within the bowl.

A substantially sealed space is formed between the buttocks of a user who has sat in order to relieve himself/herself and the aggregate of accumulated ozone-containing bubbles. However, in accordance with the present invention, the ozone-containing gas is further supplied to the space above the supplied purifying agent in the bowl. As a result, the substantially sealed space is filled with the supplied ozone-containing gas.

By using the above-described purifying method, the following action is obtained. First, because the liquid or solid excrement which has been egested from the user is covered with the purifying agent, the diffusion paths of the odor discharged from the excrement is blocked as mentioned above. Accordingly, the odor is not diffused. Further, when each of the ozone-containing bubbles is disappeared, the ozone-containing membrane of the ozone-containing bubble is applied to and permeates through the excrement as ozone water having deodorization/sterilization action. Thus, the excrement is deodorized and sterilized. Moreover, when each of the ozone-containing bubbles has disappeared, the ozone-containing gas which is contained within the ozone-containing membrane and has deodorization/sterilization action is released and diffused. As a result, the odor which has been already discharged from the excrement is deodorized by the ozone-containing gas.

Additionally, in the present invention, since the ozone-containing gas is kept within the substantially sealed space formed between the seated user's buttocks and the aggregate of accumulated ozone-containing bubbles, the gas which has been discharged from the user at the time of egesting is effectively deodorized by the ozone-containing gas. Further, since the user's buttocks contact the ozone-containing gas, the skin of the user which is in the vicinity of the anus is sterilized. In particular, when the aged, the handicapped, medical patients, or the like use the toilet, it may take a relatively long time to relive himself/herself or there may be a large amount of gas discharged. In this case, the deodorization/sterilization action by supplying the ozone-containing gas is regarded as effective.

BRIEF DESCRIPTION OF THE DRAWINGS

FIG. 6 is a schematic structural view which shows an embodiment in which a purifying method using the purifying agent is applied to a toilet.

PREFERRED MODE FOR CARRYING OUT THE INVENTION

An embodiment of the present invention will be explained hereinafter by using FIGS. 1 through 5.

Figure 1:
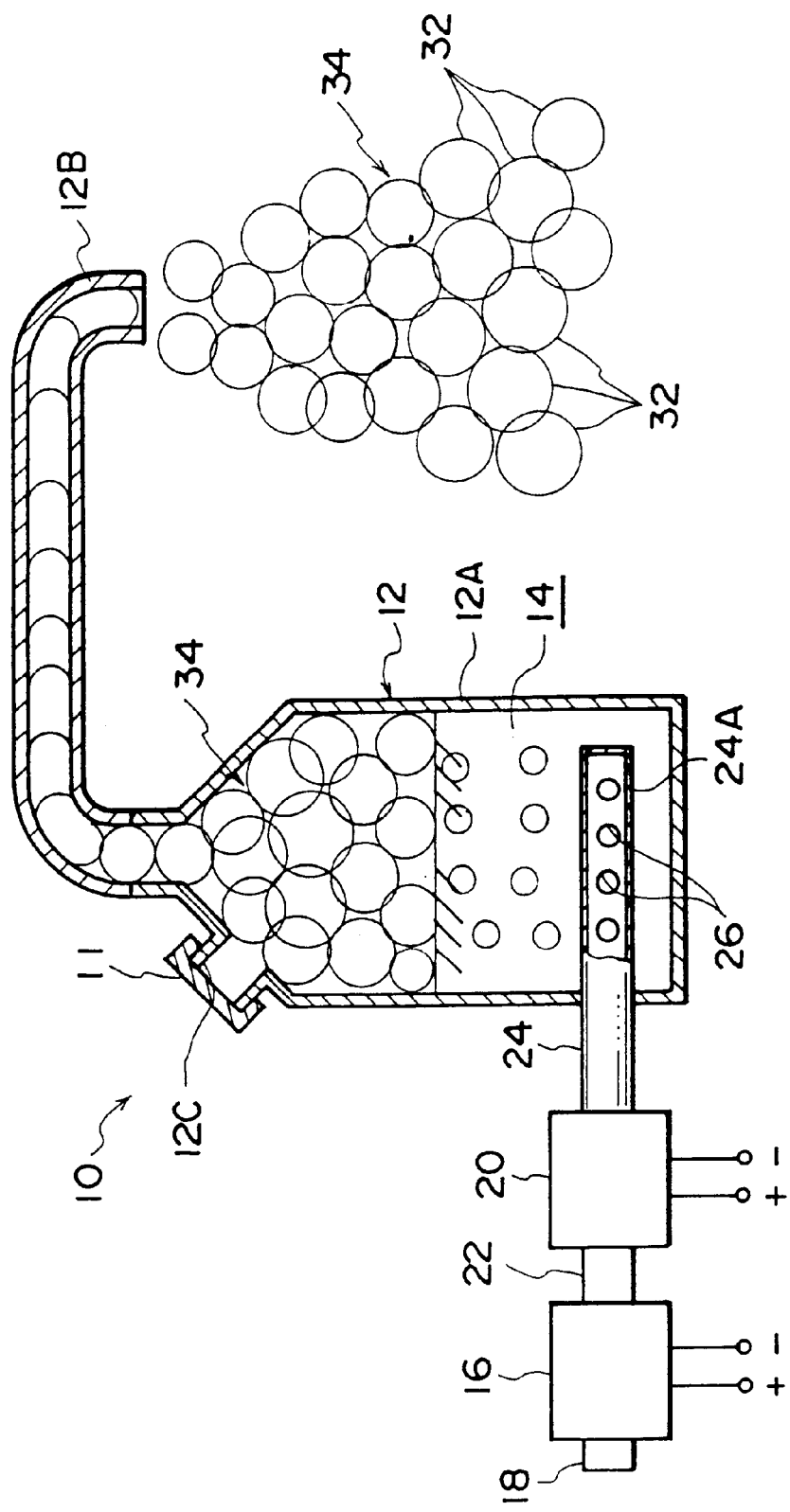
FIG. 1 is a structural view which shows the schematic structure of a purifying agent generating apparatus relating to a present embodiment.
Figure 2:
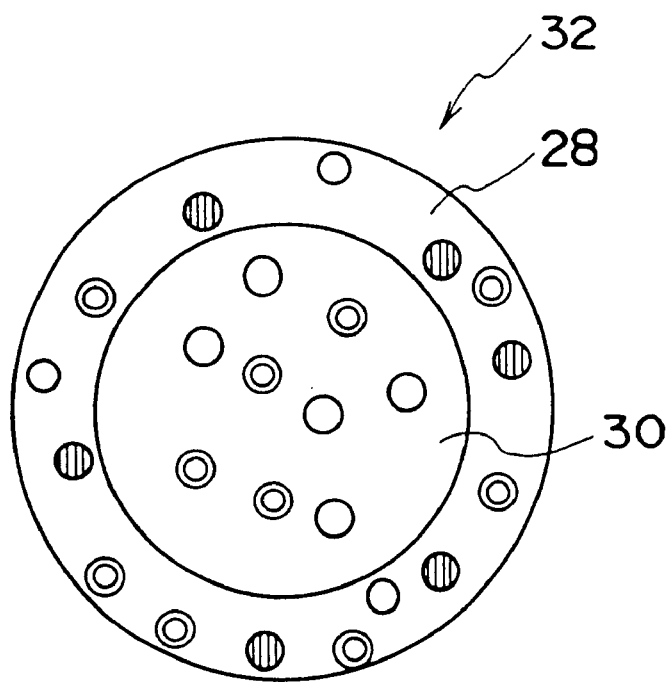
FIG. 2 is a typical view which shows the structure of an ozone- containing bubble of a purifying agent which has been generated by the purifying agent generating apparatus shown in FIG. 1.

FIG. 1 shows the schematic structure of a purifying agent generating apparatus 10 relating to the present embodiment. As shown in FIG. 1, the purifying agent generating apparatus 10 includes a container 12. The container 12 comprises a cylindrical (tank-shaped) main body portion 12A having a bottom, a discharge portion 12B which extends outwardly in the radial direction from the upper end central portion of this main body portion 12A and whose distal end portion directs toward the lower side portion of the apparatus, and a solution replenishing port 12C which is provided at a predetermined position of an upper end portion of the main body portion 12A and is closed by a cap 11.

A predetermined amount of solution 14, into which a surface-active agent has been dissolved, is contained within the main body portion 12A of this container 12. The solution 14 may be replenished manually into the main body portion 12A from the solution replenishing port 12C or may be replenished automatically into the main body portion 12A by connecting an unillustrated solution replenishing device to the solution replenishing port 12C.

Further, it is preferable that the surface-active agent used in the present embodiment does not react or hardly reacts with ozone. Under the conditions of selection, from the viewpoints of ozone stability and surface-active agent stability, a surface-active agent which belongs to an unsaturated hydrocarbon compound is not preferable and a surface-active agent which belongs to a saturated hydrocarbon compound is preferable. From the viewpoints of operation suitability under the acid conditions, an anionic (negative ion) surface-active agent or a nonionic (non-ion) surface-active agent is preferable due to the stability within an acid solution, and a cationic (positive ion) surface-active agent is not preferable. In particular, the anionic surface-active agent (alkyl sulfate, polyoxyethylene alkyl ether sulfate, sulfosuccinate, sarcosinate, amide ether sulfate, monoester, diester, carboxylate, ether carboxylate, alkyl benzene sulfonate, palm oil fatty acid sodium methyl taurine, or the like) is considered more suitable.

On the other hand, an ozone gas generator 16 which generates ozone gas by operation is disposed at a predetermined position of the outer side of the aforementioned container 12. A suction port 18 for sucking air which is opened to the atmosphere is formed at one side portion of the ozone gas generator 16. The ozone gas generator 16 which can be used includes a generator (ozonizer) which effects silent electric discharge in clean dry air or oxygen, a generator which uses an $O_3$ lamp, or the like.

An air pump 20 is disposed between this ozone gas generator 16 and the container 12. One end portion of a suction pipe 22 is connected to one side portion of the air pump 20 and another end portion thereof is connected to another side portion of the ozone gas generator 16. Accordingly, the ozone gas generator 16 and the air pump 20 are communicated with each other via the suction pipe 22. Further, another side portion of the air pump 20 is connected to one end portion of a supply pipe 24. The intermediate portion of this supply pipe 24 penetrates through a side wall of the main body portion 12A and another end portion thereof is disposed directly above a bottom wall of the main body portion 12A. Further, a number of gas supply holes 26 are formed on the circumferential surface of the other end portion of the supply pipe 24. Consequently, the air pump 20 and the main body portion 12A of the container 12 are communicated with each other via the supply pipe 24. The other end portion of the supply pipe 24, on which the number of gas supply holes 26 are formed, functions as a nozzle which blows ozone gas into the solution 14. Accordingly, the other end portion will be hereinafter referred to as "nozzle 24A".

Next, the operation and effect of the present embodiment will be explained.

First, a predetermined amount of the solution 14 is replenished manually or automatically into the main body portion 12A from the solution replenishing port 12C of the container 12. Next, the purifying agent generating apparatus 10 is operated. In this way, first, ozone gas is generated by the ozone gas generator 16. The generated ozone gas is sucked into the air pump 20 via the suction pipe 22 of the air pump 20 and blown into the solution 14 from the nozzle 24A via the supply pipe 24.

In this way, a portion of ozone gas is dissolved into the solution 14, into which the surface-active agent has been dissolved, and the ozone gas which has not been dissolved into the solution 14 goes up toward the surface of the solution 14 as gas. As a result, a purifying agent 34 is formed on the surface of the solution 14. The purifying agent 34 is formed by an aggregate of ozone-containing bubbles 32 (see the typical view in FIG. 2) and each of the ozone-containing bubbles 32 includes an ozone-containing membrane 28, into which ozone has been dissolved, and ozone-containing gas 30, which is contained within this ozone-containing membrane 28 and is a mixed gas of ozone and air.

When the above-described purifying agent is generated, the type and concentration of the surface-active agent and the amount of ozone gas supplied are properly selected. Accordingly, the amount of generation of the ozone-containing bubbles 32, the size of each of the ozone-containing bubbles 32, and the like are arbitrarily controlled to the optimal amount, size, and the like.

The purifying agent 34 (the aggregate of ozone-containing bubbles 32), which has been generated as described above, is successively pushed up within the main body portion 12A of the container 12 and discharged from the distal end portion of the discharge portion 12B. The purifying agent 34 is used, for example, as follows.

Figure 3A:
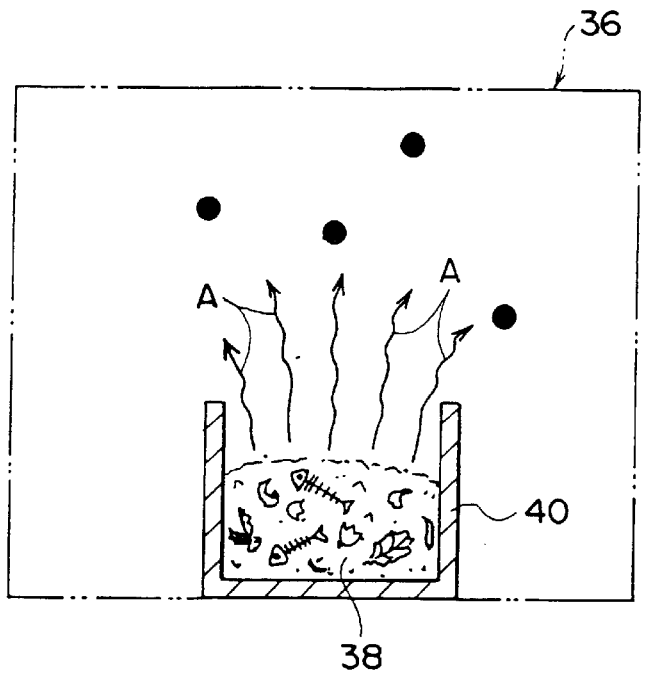
FIGS. 3A and 3B is an explanatory view for explaining the action of the purifying agent relating to the present embodiment.
Figure 3B:
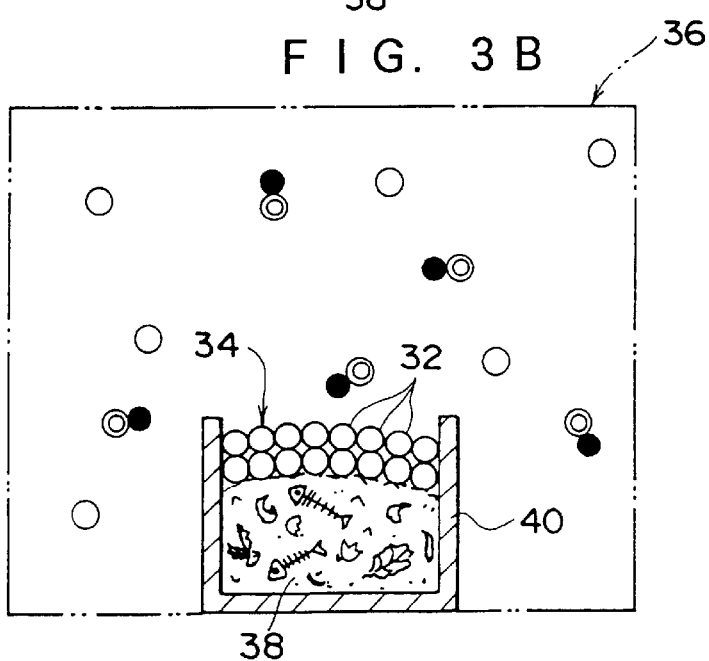

FIG. 3A shows a state in which a container 40, which contains garbage 38, is placed within a hypothetical closed space 36 of a sanitary installation or waste disposal facility. In this state, as shown in FIG. 3B, the purifying agent 34 which has been generated as described above is dispersed in layers on the garbage 38 within the container 40 (the layers of purifying agent 34 are formed).

When the surface of the garbage 38 is covered with the aggregate of ozone-containing bubbles 32, the diffusion paths of odor (shown by arrows A in FIG. 3A), which is a rotten odor and discharged from the garbage 38, are blocked. Thus, the odor is not diffused. Since the dispersed purifying agent 34 is generated on the basis of the solution into which the surface-active agent has been dissolved, the purifying agent 34 stays for a relatively long time such that the state in which the diffusion paths of odor are blocked is maintained.

Further, when each of the ozone-containing bubbles 32 has disappeared, the ozone-containing membrane 28 of the ozone-containing bubble 32 is applied to and permeates through the garbage 38 as ozone water having deodorization/sterilization action. Accordingly, the garbage 38 itself is deodorized and sterilized.

Further, when each of the ozone-containing bubbles 32 has disappeared, the ozone-containing gas 30, which is contained within the ozone-containing membrane 28 and has deodorization/sterilization action, is released and diffused. As a result, the odor which has been already discharged from the garbage 38 and remains is also deodorized by the diffused ozone-containing gas 30 (deodorized by oxidative deodorization reaction).

Namely, in accordance with the present embodiment, deodorization/sterilization action formed by three processes, i.e., blocking of the diffusion paths of odor before the bubbles have disappeared, deodorization/sterilization action by the ozone water in the ozone-containing membrane 28 after the bubbles have disappeared, and deodorization by the ozone-containing gas 30 after the bubbles have disappeared, is obtained. Therefore, in accordance with the present embodiment, purification performance can be improved.

Further, as is found from the aforementioned process for generating the purifying agent 34, when the purifying agent generating apparatus 10 relating to the present embodiment is used, it is easy to generate the purifying agent 34 formed by the aggregate of ozone-containing bubbles 32, each of which comprises the ozone-containing membrane 28 and the ozone-containing gas 30.

Next, reference will be made to the test results of the purifying agent 34 which has been generated by the purifying agent generating apparatus 10 relating to the present embodiment.

[Structure of Testing Device]

Figure 4:
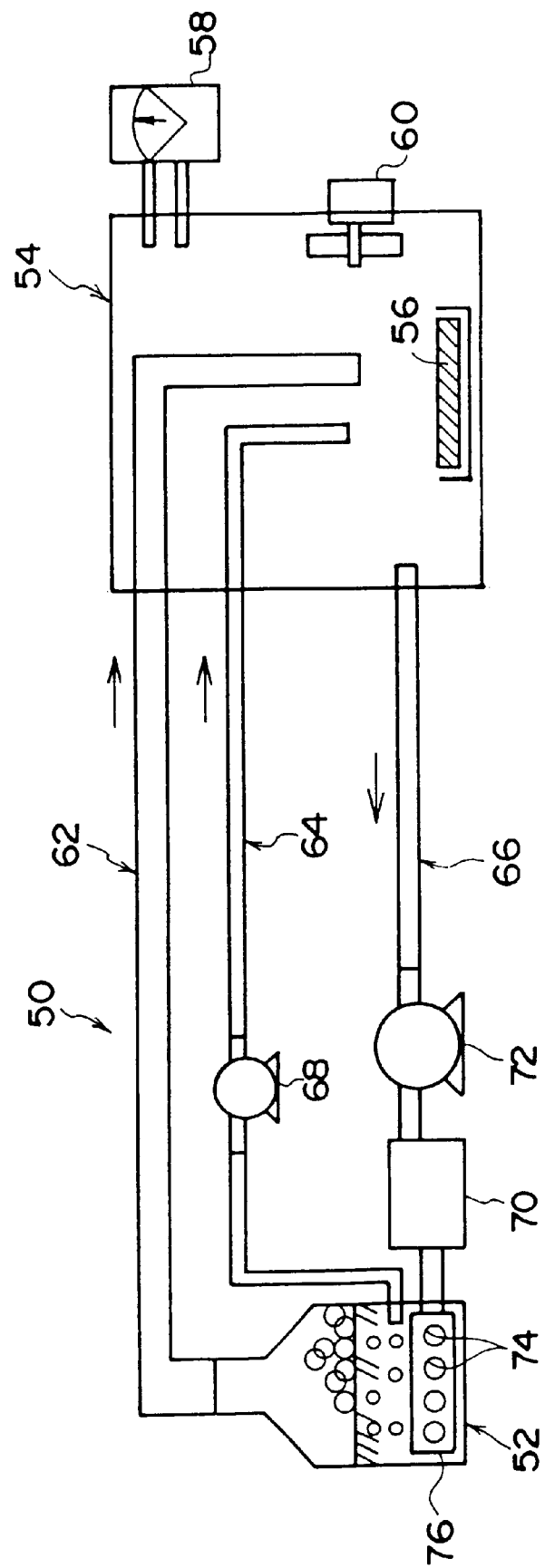
FIG. 4 is a schematic structural view of a testing device for testing the effect of the purifying agent relating to the present embodiment.

As shown in FIG. 4, a testing device 50 includes a device 52 for generating a purifying agent or the like and a sealed container 54. A sponge 56, which is impregnated with a certain amount of $H_2S$ solution having a certain concentration, is disposed on the bottom portion of the sealed container 54. Further, a concentration meter 58 for measuring the concentration of the $H_2S$ gas is provided at the side wall upper portion of the sealed container 54. Further, a stirring fan 60 is attached to the side wall lower portion of the sealed container 54.

The aforementioned sealed container 54 and the device 52 for generating a purifying agent or the like are communicated with each other through three supply lines, i.e., a first pipe line 62, a second pipe line 64, and a third pipe line 66. The first pipe line 62 is a line which directly communicates the upper end portion of the device 52 for generating a purifying agent or the like and an internal space of the sealed container 54. Further, an ozone water supply pump 68 is provided in the middle of the second pipe line 64. Moreover, an ozone gas generator 70 and an air pump 72 are provided in the middle of the third pipe line 66. Still further, a nozzle 76, in which a number of gas supply holes 74 are formed, is disposed within the device 52 for generating a purifying agent or the like which is connected to the third pipe line 66.

[Method of Test]

In the test, the sponge 56 impregnated with a certain amount of $H_2S$ solution having a certain concentration was placed on the bottom portion of the sealed container 54 and the stirring fan 60 of the sealed container 54 was operated for a certain time (e.g., five minutes). Thereafter, the object of evaluation was generated within the device 52 for generating a purifying solution or the like and supplied into the sealed container 54. Changes in the concentration of $H_2S$ with time were measured.

[Results of Test]

Figure 5:
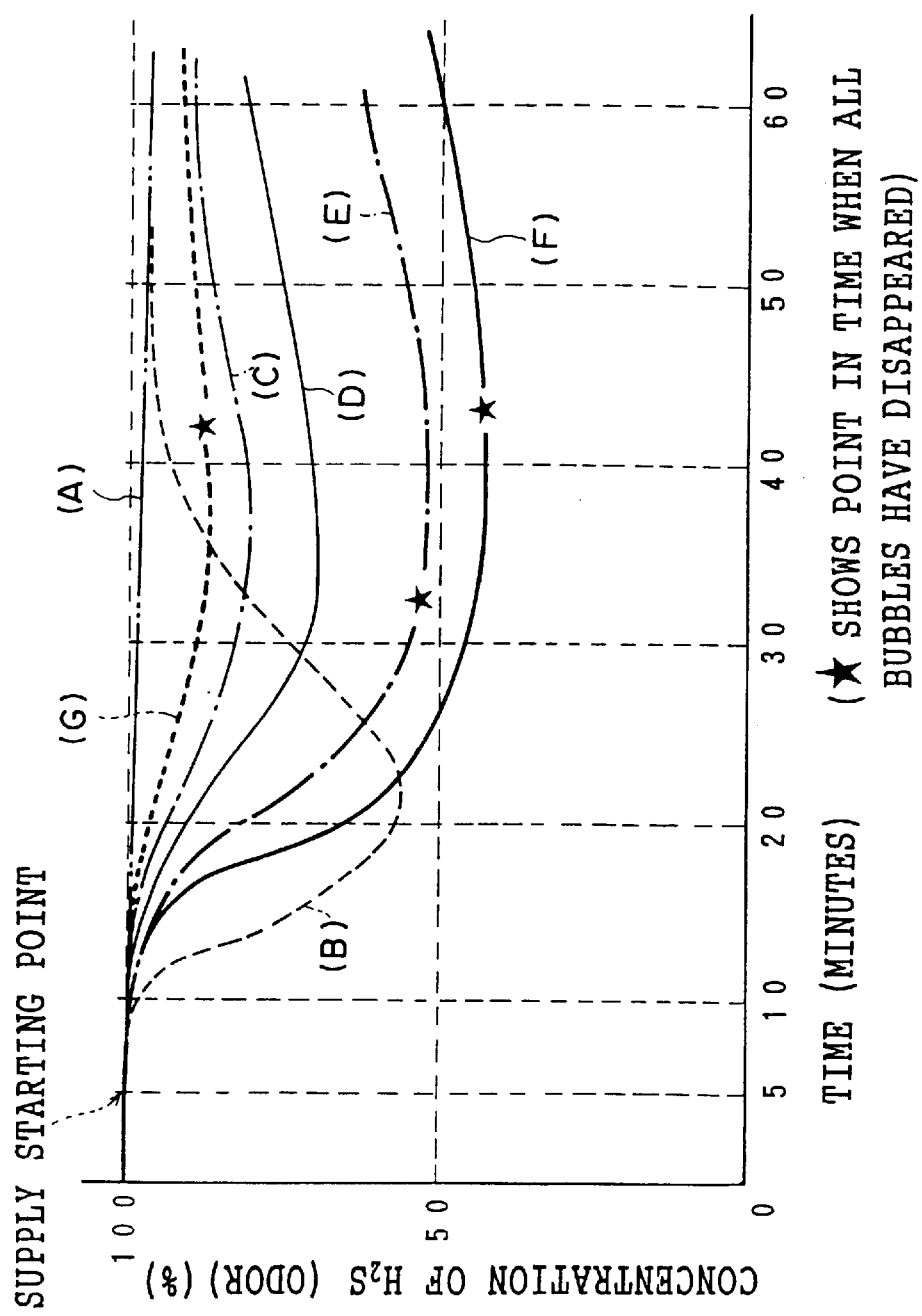
FIG. 5 is data which shows the results of test using the testing device shown in FIG. 4.

Graph (A) shown in FIG. 5 shows the result when nothing was placed into the sealed container 54. Namely, the graph (A) shows the result when all of the first pipe line 62 through the third pipe line 66 were stopped. In this case, even if 60 minutes have passed since the point in time when the test started (0 minute), hardly any change in the concentration of $H_2S$ (odor) was seen and the concentration remained at about 100%.

Graph (B) shows the result when ozone gas was supplied into the sealed container 54 for a predetermined time (five minutes). Namely, the graph (B) shows the result when only the third pipe line 66 and the first pipe line 62 were operated under predetermined conditions. When nothing was placed in the device 52 for generating a purifying agent or the like and the third pipe line 66 was operated, only ozone gas was generated within the device 52 for generating a purifying agent or the like. This ozone gas was supplied without any alteration thereto into the sealed container 54 through the first pipe line 62 for only a predetermined time (five minutes).

In this case, because the deodorization effect against $H_2S$ (odor), which has been already generated and fills the sealed container 54, was obtained, the concentration of $H_2S$ (odor) was lowered desirably for about 20 minutes since the point in time when the concentration was measured. However, because the deodorization reaction finished afterwards, the effect did not continue. It was found that the concentration returned to substantially the original state after 40 minutes have passed since the point in time of measurement.

Graph (C) shows the result when a predetermined amount (10 cc) of ozone water was injected into the sealed container 54. Namely, the graph (C) shows the result when only the third pipe line 66 and the second pipe line 64 were operated under predetermined conditions. When only water was injected into the device 52 for generating a purifying agent or the like and the third pipe line 66 was operated, ozone water was generated within the device 52 for generating a purifying agent. Only the predetermined amount (10 cc) of ozone water was injected without any alteration thereto into the sponge 56 in the sealed container 54 through the first pipe line 62.

In this case, since the ozone water was permeated through the sponge 56 serving as a source of odor within the sealed container 54, a deodorization/sterilization effect was obtained. However, a deodorization effect was not obtained against $H_2S$ (odor) which has already been generated and fills the sealed container 54. Therefore, the concentration of $H_2S$ (odor) lowered to some extent after a period of time had passed, however, a satisfactory result was not obtained.

Graph (D) shows a result in which a predetermined amount (20 cc) of ozone water was injected into the sealed container 54. This shows the result when the test was carried out in the same way as the test for graph (C) and the amount of ozone water injected was twice that in the case of graph (C).

In this case, since the test conditions were the same except for the amount of ozone water injected, the configurations of the graphs were likely to be the same. However, since the amount of ozone water injected in the case of graph (D) was twice that in the case of graph (C), it was found that the concentration of $H_2S$ (odor) reduced was substantially twice that in the case of graph (C). However, the concentration of $H_2S$ (odor) reduced was substantially the same and a satisfactory result was not yet obtained.

Graph (E) shows the result when a predetermined amount (10 cc) of purifying agent relating to the present embodiment was supplied into the sealed container 54. Namely, the graph (E) shows the result when only the third pipe line 66 and the first pipe line 62 were operated under predetermined conditions. When the solution, into which the surface-active agent has been dissolved, was placed into the device 52 for generating a purifying agent or the like and the third pipe line 66 was operated, the aforementioned ozone-containing bubbles were generated within the device 52 for generating a purifying agent or the like. Only the predetermined amount (10 cc) of ozone-containing bubbles without any alteration thereto were supplied into the sealed container 54 through the first pipe line 62.

In this case, the sponge 56 serving as a source of odor was covered in layers of the purifying agent formed by the aggregate of ozone-containing bubbles. Accordingly, the aforementioned deodorization/sterilization action formed by three processes was obtained. Namely, the diffusion paths of odor from the sponge 56 were blocked, the deodorization/sterilization action was obtained by the application/permeation of ozone water within the ozone-containing membranes of the disappeared ozone-containing bubbles, and deodorization action by the ozone-containing gas within the disappeared ozone-containing bubbles was performed against the $H_2S$ (odor) which had been already generated and filled the sealed container 54. Accordingly, the concentration of $H_2S$ (odor) was reduced by half and a sufficient effect was obtained. Further, because the purifying agent was the aggregate of ozone-containing bubbles, it was found that the effect was continuous even after 60 minutes have passed.

Graph (F) shows the result when a predetermined amount (20 cc) of purifying agent relating to the present embodiment was supplied into the sealed container 54. This shows the result when the test was carried out in the same way as that for graph (E) and the amount of supply of purifying agent formed by the aggregate of ozone-containing bubbles was twice that in the case of graph (E).

In this case, since the test conditions were the same except for the amount of purifying agent supplied, the configurations of the graphs were likely to be the same. However, since the amount of ozone water injected in the case of graph (F) was twice that in the case of graph (E), it was found that the concentration of $H_2S$ (odor) reduced was further accelerated. Therefore, extremely good results were able to be obtained.

Graph (G) shows the result when a predetermined amount (20 cc) of bubbles which do not contain ozone is supplied into the sealed container 54. Namely, the graph (G) shows the result when only the third pipe line 66 and the first pipe line 62 were operated under predetermined conditions. When the solution, into which the surface-active agent had been dissolved, was placed into the device 52 for generating a purifying agent or the like and the third pipe line 66 was operated in a state in which the ozone gas generator 70 was not operated, plain bubbles were generated within the device 52 for generating a purifying agent or the like. Only a predetermined amount (20 cc) of bubbles without any alteration thereto was supplied into the sealed container 54 through the first pipe line 62.

In this case, because the bubbles themselves did not have any deodorization/sterilization action, the concentration of $H_2S$ (odor) was slightly lower than that of the aforementioned graph (A). Therefore, the results were not satisfactory. The slight reduction of concentration of the $H_2S$ (odor) was caused by the fact that the sponge 56 was covered with the layers of bubbles and the diffusion paths of odor were blocked until the bubbles disappeared.

From the above-described test results, it was found that the test examples relating to the present embodiment (the graphs (E) and (F)) were extremely effective.

In the present embodiment, an example is described of a case in which both deodorization and sterilization are effected by using the purifying agent 34. However, the present invention is not limited to this and the purifying agent 34 relating to the present embodiment may be used for the purpose of either one of deodorization and sterilization.

Further, "sterilization" in the fourth embodiment includes sterilization-washing. Namely, if a surface-active agent (the aforementioned surface-active agent) which is harmless to human body is selected, the present invention can be applied to sterilization-washing (or sterilization-washing combined with deodorization) of cooking appliances and table wares used in a kitchen, sterilization-washing of cooks' hands, sterilization-washing of hands after using the toilet, or the like. In this case, the sterilization effect is the same as that when washing is carried out with water in detergent or the like, while the amount of water used is approximately $\frac{1}{100}$ thereof.

Next, a description will be given using FIG. 6 of an embodiment in which a purifying method using the aforementioned purifying agent 34 is applied to a toilet.

A toilet 80 includes a box-shaped container main body 82. An opening 84, which has a predetermined configuration when viewed from above, is formed at a top wall portion 82A of the container main body 82 and a seat 86 is disposed at the periphery of the opening 84. Moreover, an unillustrated seat cover is disposed at the top wall portion 82A of the container main body 82 so as to be rotatable around a supporting shaft. A bowl-shaped toilet bowl 88, whose upper end portion is fixed to the reverse surface side of the top wall portion 82A, is disposed beneath the opening 84 in the container main body 82. In the case of an ordinary flush toilet, the lower end portion of the bowl 88 is connected to an unillustrated drainpipe. In the case of a portable toilet, the lower end portion of the stool 88 is connected to an unillustrated excrement containing tank which is disposed below the bowl 88 in the container main body 82.

Moreover, the aforementioned purifying agent generating apparatus 10 is built in the above-described container main body 82. Because the structures of respective portions of the purifying agent generating apparatus 10 are basically the same as those shown in FIG. 1, portions are denoted by the same reference numerals and descriptions thereof are omitted. Only portions which are different from those shown in FIG. 1 will be explained.

In the present embodiment, in order to supply ozone-containing gas (in FIG. 6, gas is referred to as "$O_3$" for convenience) after the supply of the purifying agent 34, a three-way valve 90 is disposed in the middle of a supply tube 24 which connects an air pump 20 and a container 12. Further, a discharge portion of the container 12 and the predetermined position of an upper portion of the bowl 88 are connected by a purifying agent supply tube 92, and the three-way valve 90 and the predetermined position of the purifying agent supply tube 92 are connected by an ozone-containing gas supply tube 94. When the three-way valve 90 is opened, the supply line to the ozone-containing gas supply tube 94 is closed. In contrast, when the three-way valve 90 is closed, the supply line to the purifying agent supply tube 92 is closed. At the predetermined position of the upper portion of the bowl 88, a plurality of discharge ports are formed at predetermined intervals. In the above-described structure, the three-way valve 90 and the ozone-containing gas supply tube 94 serve as ozone-containing gas supply means in a broad sense.

Further, an unillustrated seat cover sensor (in a broad sense, serving as means of detecting a state immediately before a toilet is used) for detecting the opening of the seat cover is disposed at the container main body 82. The seat cover sensor is connected to an unillustrated controller such that the operation of the purifying agent generating apparatus 10 including opening and closing operation of the three-way valve 90 is controlled on the basis of the detection signal from the seat cover sensor.

In accordance with the above-described structure, when a user opens the seat cover, the seat cover sensor detects the opening of the seat cover. When the seat cover is opened, the purifying agent generating apparatus 10 is operated by the controller in a state in which the three-way valve 90 is opened. In this way, the ozone-containing gas is injected into the container 12 and the purifying agent 34 is generated. A predetermined amount (approximately $\frac{1}{4}$ to $\frac{1}{2}$ of the volume of the bowl 88) of the purifying agent 34 generated is supplied into the bowl 88 through the purifying agent supply tube 92. In this way, the aggregate of the purifying agent 34, i.e., ozone-containing bubbles, is accumulated within the bowl 88.

In this state, the user sits on the seat 86 in order to relieve himself/herself. Accordingly, a substantially sealed space 98 is formed between the user's buttocks 96 and the purifying agent 34 which has been already accumulated. At this time, the three-wave valve 90 is switched to a closed state and the purifying agent generating apparatus 10 is continuously operated for a predetermined time by the controller. In this way, the ozone-containing gas ($O_3$) is further supplied to the space 98 which is provided above the supplied purifying agent 34 within the bowl 88. The specific gravity of the supplied ozone-containing gas is heavier than that of air such that the gas fills the above-described substantially sealed space 98.

The following actions are obtained by effecting the above-described purifying method. First, because a liquid or solid excrement 100 egested by the user is covered by the purifying agent 34, the diffusion paths of odor discharged from the excrement 100 are blocked as mentioned hereinbefore. Thus, the odor is not diffused. Further, when each of the ozone-containing bubbles has disappeared, the ozone-containing membrane of the ozone-containing bubble is applied to and permeates through the excrement 100 as ozone water having deodorization/sterilization action. Accordingly, the excrement 100 is deodorized and sterilized. Moreover, when each of the ozone-containing bubbles has disappeared, the ozone-containing gas, which is contained within the ozone-containing membrane and has deodorization/sterilization action, is released and diffused. As a result, the odor which has been already discharged from the excrement 100 is deodorized by the ozone-containing gas.

In addition, since the ozone-containing gas fills the substantially sealed space 98 formed between the seated user's buttocks 96 and the accumulated purifying agent 34, the gas which has been discharged from the user at the time of egesting or the like is also effectively deodorized by the ozone-containing gas. Further, because the user's buttocks 96 contact the ozone-containing gas, the skin of the user which is in the vicinity of the anus is also sterilized. In particular, when the aged, the handicapped, medical patients, or the like use a toilet, it may take a relatively long time to relive himself/herself or there may be a large amount of gas discharged. In this case, the deodorization/sterilization action by supplying the ozone-containing gas is effective.

Accordingly, extremely high purifying performance can be obtained by applying the purifying method relating to the present embodiment to the toilet 80.

In the embodiment shown in FIG. 6, a structure is used in which the seat cover sensor detects the opening of the seat cover and thereby the purifying agent generating apparatus 10 is operated. However, the present invention is not limited to this and any detection means may be used provided that the detection means can detect a state immediately before a user uses the toilet 80. For example, a structure may be used in which a sitting sensor which detects that a user has taken the seat 86 is used and thereby the purifying agent generating apparatus 10 is operated. Further, in addition to the structure which automatically detects the state immediately before a user uses the toilet 80, a structure may be used in which a user presses an operation switch and thereby the purifying agent generating apparatus 10 is operated.

Further, in the embodiment shown in FIG. 6, a structure is possible in which the supply line of the purifying agent 34 and the supply line of the ozone-containing gas are joined at the end and the purifying agent 34 and the ozone-containing gas are supplied from the same discharge port. However, the present invention is not limited to this. A structure may be used in which a generation/supply line of the purifying agent 34 and a generation/supply line of the ozone-containing gas are separately provided.

Further, in the embodiment shown in FIG. 6, the method is used in which the ozone-containing gas is continuously supplied into the bowl 88 for a predetermined time. However, the present invention is not limited to this and a method may be used in which the ozone-containing gas is supplied intermittently.

As described above, the purifying agent relating to the first aspect of the present invention is formed by the aggregate of ozone-containing bubbles and each of the bubbles has an ozone-containing membrane, into which ozone has been dissolved, and ozone-containing gas, which is contained in the ozone-containing membrane and includes ozone. Accordingly, the aforementioned deodorization/sterilization action formed by three processes is obtained. As a result, a superior effect is achieved in that purifying performance can be improved.

The apparatus for generating a purifying agent relating to the second aspect of the present invention includes the container, the ozone gas generating means, and the ozone gas supply means. The container contains the solution into which a surface-active agent has been dissolved, the ozone gas generating means generates ozone gas, and the ozone gas supply means communicates the ozone gas generating means and the inner portion of the container and supplies the ozone gas which has been generated by the ozone gas generating means into the solution. Consequently, a superior effect is achieved in that the purifying agent of the first aspect having higher purifying performance can be easily generated.

In the method of generating a purifying agent relating to the third aspect of the present invention, the ozone gas which has been generated by the ozone gas generating means is supplied into the solution which is contained in the container and into which the surface-active agent has been dissolved. Accordingly, a superior effect is achieved in that the purifying agent of the first aspect having a higher purifying performance can be easily generated.

In the purifying method using the purifying agent relating to the fourth aspect of the present invention, the purifying agent of the first aspect is used for carrying out at least one of deodorization and sterilization on the object of deodorization/sterilization. Accordingly, the aforementioned deodorization/sterilization action formed by three processes is effectively achieved. As a result, a superior effect is achieved in that purifying performance can be improved.

In the purifying method using the purifying agent relating to the fifth aspect of the present invention, the predetermined amount of purifying agent formed by the aggregate of the ozone-containing bubbles of the first aspect is supplied into the bowl of the toilet, and thereafter the ozone-containing gas is further supplied to the space above the supplied purifying agent in the bowl. Thus, the aforementioned deodorization/sterilization action formed by three processes is effectively achieved against liquid or solid excrement, and deodorization can be effectively achieved by the ozone-containing gas against the gas which has been discharged from the user at the time of egesting or the like. As a result, even if the method is applied to the toilet, a superior effect is achieved in that an extremely high purifying performance can be obtained.

What is claimed is:

1. A purifying agent comprising an aggregate of ozone-containing bubbles, each bubble being formed of (1) a membrane containing ozone dissolved therein, and (2) an ozone-containing gas contained within the membrane, the bubbles having been generated at the surface of an aqueous solution containing ozone and then removed from the surface of the solution.

2. The purifying agent of claim 1, wherein the bubbles and the solution each contain a surface-active agent.

3. A method of generating a purifying agent, the purifying agent being formed of an aggregate of bubbles to be applied to a target to be purified, each bubble having an ozone-containing membrane into which ozone has been dissolved, and ozone-containing gas contained in the membrane, the method comprising the steps of:

supplying ozone gas generated by an ozone gas generator into a solution which is contained within a lower portion of a container and which contains a surface-active agent so as to dissolve ozone in the solution and to generate ozone-containing bubbles on a surface of the solution;

removing the generated bubbles from the surface of the solution to form an aggregate of the bubbles; and discharging the aggregate of bubbles from the container.

4. The method of claim 3, further including the step of applying the aggregate of bubbles to a target to be purified.

5. The method of claim 3, further including the step of applying the aggregate of bubbles to an object to be sterilized and/or deodorized.

6. The method of claim 3, further including the step of supplying the aggregate of bubbles to the bowl of a toilet, and further supplying ozone-containing gas to a space above the supplied aggregate of bubbles.

7. An apparatus for generating a purifying agent, the purifying agent being formed by an aggregate of ozone-containing bubbles, each bubble having an ozone-containing membrane into which ozone has been dissolved, and ozone-containing gas which is contained within this ozone-containing membrane, the apparatus comprising:

a container which contains in a lower portion thereof a solution into which a surface-active agent has been dissolved;

an ozone gas generator which generates ozone gas;

a conduit connecting said ozone gas generator and an inner portion of said container, which supplies the ozone gas generated by said ozone gas generator into the solution to dissolve ozone in said solution and to form ozone-containing bubbles on a surface of the solution; and a pipe connected to an upper portion of the container for removing from the surface of the solution an aggregate of said bubbles and for discharging to a target to be purified the aggregate of ozone-containing bubbles formed in the container.

* * * * *

UNITED STATES PATENT AND TRADEMARK OFFICE
CERTIFICATE OF CORRECTION

PATENT NO.   : 6,485,685 B1
DATED        : November 26, 2002
INVENTOR(S)  : Tomomi Kishi et al.

It is certified that error appears in the above-identified patent and that said Letters Patent is hereby corrected as shown below:

Column 12,
Line 60, "at the surface" should read -- on the surface --.
Line 62, after "solution", insert -- as an aggregate of the bubbles --.

Column 13,
Lines 5-6, after "contained within a", delete "lower portion of a".
Line 7, after "active agent", insert a -- comma --.
Line 10, after removing", insert -- the aggregate of --.
Line 11, after "solution", delete "to form an aggregate of the bubbles".
Line 12, after "discharging the", insert -- removed --.

Column 14,
Line 1, "having" should read -- being formed of --.
Line 5, after "which contains", delete "in a lower portion thereof".
Line 18, "an aggregate" should read -- the aggregate --.

Signed and Sealed this

First Day of April, 2003

JAMES E. ROGAN
*Director of the United States Patent and Trademark Office*